United States Patent [19]
Penenberg

[11] Patent Number: 5,910,172
[45] Date of Patent: Jun. 8, 1999

[54] APPARATUS FOR, AND METHOD OF, PREPARING HIP PROSTHESIS IMPLANTATION

[75] Inventor: Brad L. Penenberg, Los Angeles, Calif.

[73] Assignee: Johnson & Johnson, New Brunswick, N.J.

[21] Appl. No.: 08/859,219

[22] Filed: May 20, 1997

[51] Int. Cl.$^6$ .................................. A61F 2/32; A61F 2/28
[52] U.S. Cl. ................................................ 623/23; 606/86
[58] Field of Search ................................. 606/86, 92, 95, 606/89, 99, 94; 623/16, 18, 23; 128/898

[56] References Cited

U.S. PATENT DOCUMENTS

| | | | |
|---|---|---|---|
| 5,683,395 | 11/1997 | Mikhail | 606/86 |
| 5,697,932 | 12/1997 | Smith et al. | 606/80 |
| 5,718,707 | 2/1998 | Mikhail | 606/96 |
| 5,755,720 | 5/1998 | Mikhail | 606/94 |
| 5,788,704 | 8/1998 | Timperley | 606/86 |

*Primary Examiner*—David J. Isabella
*Attorney, Agent, or Firm*—Ellsworth R. Roston; Fulwider Patton Lee & Utecht, LLP

[57] ABSTRACT

Each tamp in a sequence has a collar at a progressively increased distance from the bottom of a cavity in a femur relative to other tamps in the sequence. The collar on each tamp has progressively increased dimensions relative to collars on other tamps to provide a snug fit of such collar against inner walls defining the femur cavity. Bone particles are also disposed in such cavity. After the insertion of each tamp into the cavity, such tamp is driven into the cavity to pack the bone fragments in the cavity against one another, the collar and the femur inner walls. Such tamp is then removed from the cavity and the next tamp in the sequence is inserted, and driven, into the cavity. The distance for driving each tamp into the cavity may be defined by a coincidence between a marking on such tamp and the top of the femur. When the last tamp in the sequence is removed from the cavity, the cavity is filled with a binder which permeates the space between the bone particles through only a limited distance because of the tight packing of the bone particles. The prosthesis may then be properly positioned in the femur cavity. The prosthesis is slightly narrower than the last tamp so that a thin layer of the binder is formed between the prosthesis and the bone fragments. The binder hardens against the prosthesis and the bone particles to retain the prosthesis fixedly in the cavity.

33 Claims, 5 Drawing Sheets

APPARATUS FOR, AND METHOD OF, PREPARING HIP PROSTHESIS IMPLANTATION

This invention relates to apparatus for, and methods of, providing a hip prosthesis. More particularly, the invention relates to apparatus for, and methods of, providing a hip prosthesis with optimal stability over extended periods of time.

BACKGROUND OF THE INVENTION

Failure of femoral components is a recognized concern. Such hip failures have occurred for a number of different reasons. For example, individuals have suffered hip failures from awkward falls and from advancing age. Until relatively recently, individuals suffering hip failures have often been unable to walk and have often been confined to wheelchairs.

In recent years, apparatus has been developed, and techniques have been developed and refined, for implanting hip prostheses. Such apparatus and techniques have involved the insertion of a prosthesis in a cavity in a patient's femur and the bonding of the prosthesis to the femur. To improve bone quality and long term prosthesis fixation, bone particles have been inserted into the cavity and a binder has been disposed between the particles and the prosthesis in an attempt to unify them.

The hip prostheses of the prior art have been far from uniformly successful. For example, as many as ten percent (10%) of the hip prostheses have had to be repeated more than once because previous prostheses have not been successful. The failures in the hip prostheses have occurred for various reasons. One primary reason has been that the bone fragments have not been tightly packed in the femur cavity which receives the prosthesis. This has created voids in the cavity. The voids cause the bone cement to be unsupported and to crack when a force is exerted by the patient on the prothesis as by standing or walking.

U.S. Pat. No. 5,192,283 issued to Robin J. M. Ling, Graham A. Gie, W. E. Michael Mikhail, James M. Elting, Tom J. J. H. Sloof on Mar. 9, 1993, for a "System For Performing Hip Prosthesis Revision Surgery" is typical of the recent prior art. It involves problems which have caused failures in hip prostheses. One problem has been that the bone fragments have not been tightly packed in the cavity in the femur. This has created voids which constitute positions of weakness where failures in the prostheses have occurred.

BRIEF DESCRIPTION OF THE INVENTION

This invention provides apparatus for, and methods of, implanting hip prostheses, which apparatus and methods overcome the problems of the prior art. The apparatus and methods of this invention provide a tight and substantially uniform packing of bone fragments in a femur cavity so that the bone fragments become bonded to one another and to the femur. This causes forces applied to the femur to be distributed substantially uniformly throughout the femur, the prosthesis and the bone fragments between the femur and the prosthesis. Since these forces are substantially uniformly distributed, the forces at each position will be below those which produce failures in the prosthesis.

In one embodiment of the invention, each tamp in a sequence has a collar at a progressively increased distance from the bottom of a cavity in a femur relative to other tamps in the sequence. The collar on each tamp has progressively increased dimensions relative to collars on other tamps to provide a snug fit of such collar against inner walls defining the femur cavity. Bone particles are also disposed in such cavity.

After the insertion of each tamp into the cavity, such tamp is driven into the cavity to pack the bone fragments in the cavity against one another, the collar and the femur inner walls. Such tamp is then removed from the cavity and the next tamp in the sequence is inserted, and driven, into the cavity. The distance for driving each tamp into the cavity may be defined by a coincidence between a marking on such tamp and the top of the femur.

When the last tamp in the sequence is removed from the cavity, the cavity is filled with a binder which permeates the space between the bone particles through only a limited distance because of the tight packing of the bone particles. The prosthesis may then be properly positioned in the femur cavity. The prosthesis is slightly narrower than the last tamp so that a thin layer of the binder is formed between the prosthesis and the bone fragments. The binder hardens against the prosthesis and the bone particles to retain the prosthesis fixedly in the cavity.

DETAILED DESCRIPTION OF THE INVENTION

In one embodiment of the invention, a femur generally indicated at 10 is provided. The femur 10 is provided with a cavity 12 for receiving a prosthesis generally indicated at 14 in FIG. 5.

The cavity 12 is provided in successive horizontal planes with horizontal or lateral dimensions which increase at progressive distances upwardly from the bottom of the cavity. Furthermore, the shape of the cavity 12 in these successive planes may change as from a circle to a shape approaching a rectangle. This may be seen from a comparison of the sections in FIGS. 7, 8, 9 and 10.

A plug 15 (FIGS. 11, 12, 13 and 14) is disposed at the bottom of the cavity 12. A plurality of cancerous bone fragments or morsels 16 are also disposed in the cavity 12 above the plug 15. The cancerous bone fragments preferably are irregularly shaped and are preferably provided with dimensions in the order of two millimeters (2 mm) to three millimeters (3 mm).

Figure 13:
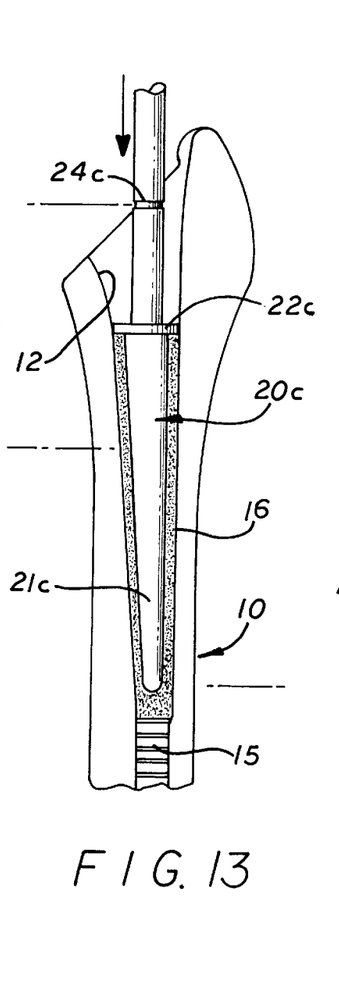
FIG. 13 is an enlarged fragmentary elevational view showing the disposition in the femur cavity of a third one of the tamps in the sequence and showing the packing of the bone fragments by such tamp to an even further increased height in the cavity.
Figure 13A:
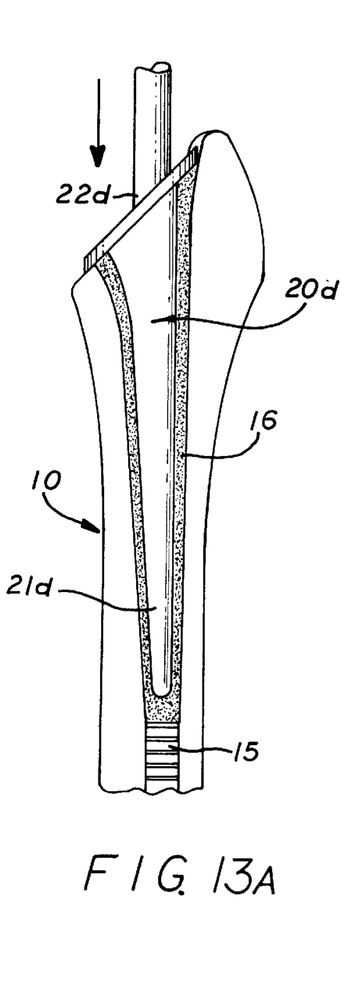
FIG. 13A is an enlarged fragmentary elevational view showing the disposition in the femur cavity of a fourth one of the tamps in the sequence and showing the packing of bone fragments to the top of the femur by such tamp.

A plurality of tamps generally indicated at 20a (FIG. 11), 22b (FIG. 12), 22c (FIG. 13) and 22d (FIG. 13A) are constructed to be disposed in sequence in the cavity 12 to pack the bone fragment in the cavity. Each of the tamps 20a, 20b, 20c and 20d may be made from a suitable material such as a stainless steel. Although four tamps 20a, 20b, 20c and 20d are illustratively provided in one embodiment of the invention, it will be appreciated that any number of tamps (more than one) may be provided without departing from the scope of the invention.

Each of the tamps 20a, 20b, 20c and 20d may be constructed in a similar manner. For example, the tamps 20a, 20b, 20c and 20d are respectively provided with shafts 21a, 21b, 21c and 21d and are also respectively provided with collars 22a, 22b, 22c and 22d at an intermediate position along the lengths of the shafts. However, the dimensions of each of the shafts 21a, 21b, 21c and 21d are different from the dimensions of the other ones of the shafts.

For example, the over-all length of the shaft 21a may be greater than the over-all length of the shaft 21b and the over-all length of the shaft 21b may be greater than the over-all length of the shaft 21c. However, the distance of the collar 22a from the bottom tip of the shaft 21a may be less than the distance of the collar 22b from the bottom tip of the shaft 21b. Similarly, the distance of the collar 22b from the bottom tip of the shaft 21b may be less than the distance of the collar 22c from the bottom tip of the shaft 21c. The collar 22d is disposed at the top of the femur 10 when the tamp 22d is inserted in the cavity 12. As will be seen, the collar 22d is angled to correspond to the angle generally encountered at the top of the femur.

The horizontal or lateral dimensions of the collar 22a on the tamp 20a are less than the horizontal or lateral dimensions of the collar 22b on the tamp 20b and the horizontal or lateral dimensions of the collar 22b are in turn less than the lateral dimensions of the collar 22c on the tamp 20c. This may be seen from a comparison of the sectional areas in FIGS. 7, 8, 9 and 10. The collars 22a, 22b, 22c and 22d are respectively intended to be disposed at progressive positions closer to the bottom of the cavity 12. At the respective positions of the collars 22a, 22b, 22c and 22d in the cavity 12, the collars are provided with horizontal or lateral dimensions to fit snugly against the femur inner walls defining the cavity 12 when the tamps are centered in the cavity.

Each of the tamps 20a, 20b, 20c and 20d is respectively provided with a marking such as a groove 24a (FIG. 11), 24b (FIG. 12), 24c (FIG. 13) and 24d (FIG. 13A) for indicating when the tamp has been driven the proper distance into the cavity 12. Each of the grooves 24a, 24b and 26c is disposed at an individual position on the shafts 21a, 21b and 21c between the associated one of the collars 22a, 22b and 22c and the top of the tamp on which the groove is located. For example, the distance between the groove 24a and the collar 22a on the tamp 20a is greater than the distance between the groove 24b and the collar 22b on the tamp 20b. The distance between the grooves 24a, 24b and 24c and the bottom ends of the tamps 20a, 20b and 20c is substantially constant.

Figure 1:
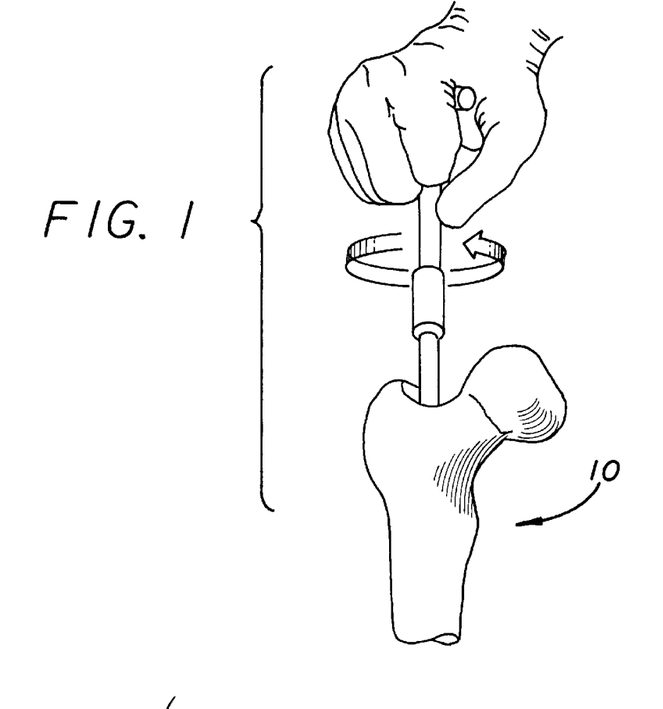
FIG. 1 is a schematic perspective view of a femur in a hip and of apparatus for producing a cavity in the femur.
Figure 2:
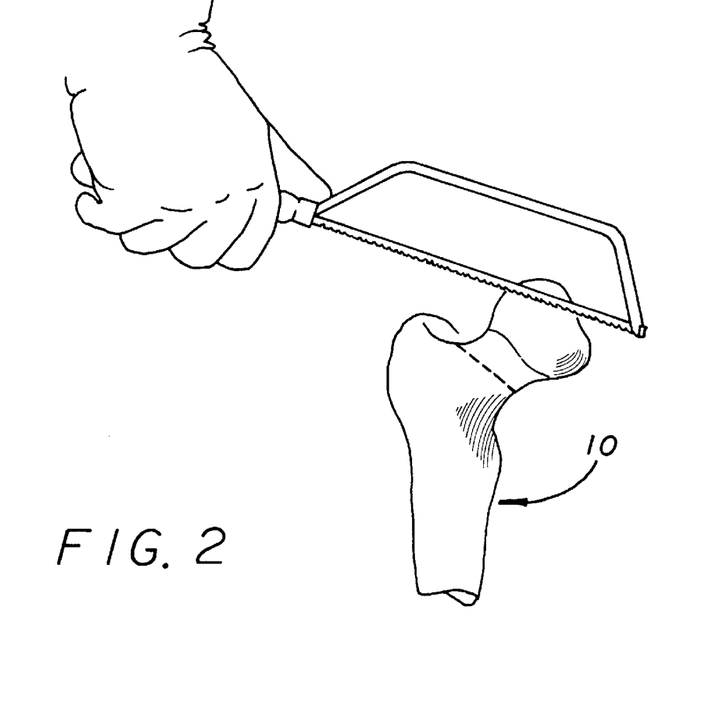
FIG. 2 is a schematic perspective view of apparatus for removing a portion of a bone at the top of the femur.
Figure 3:
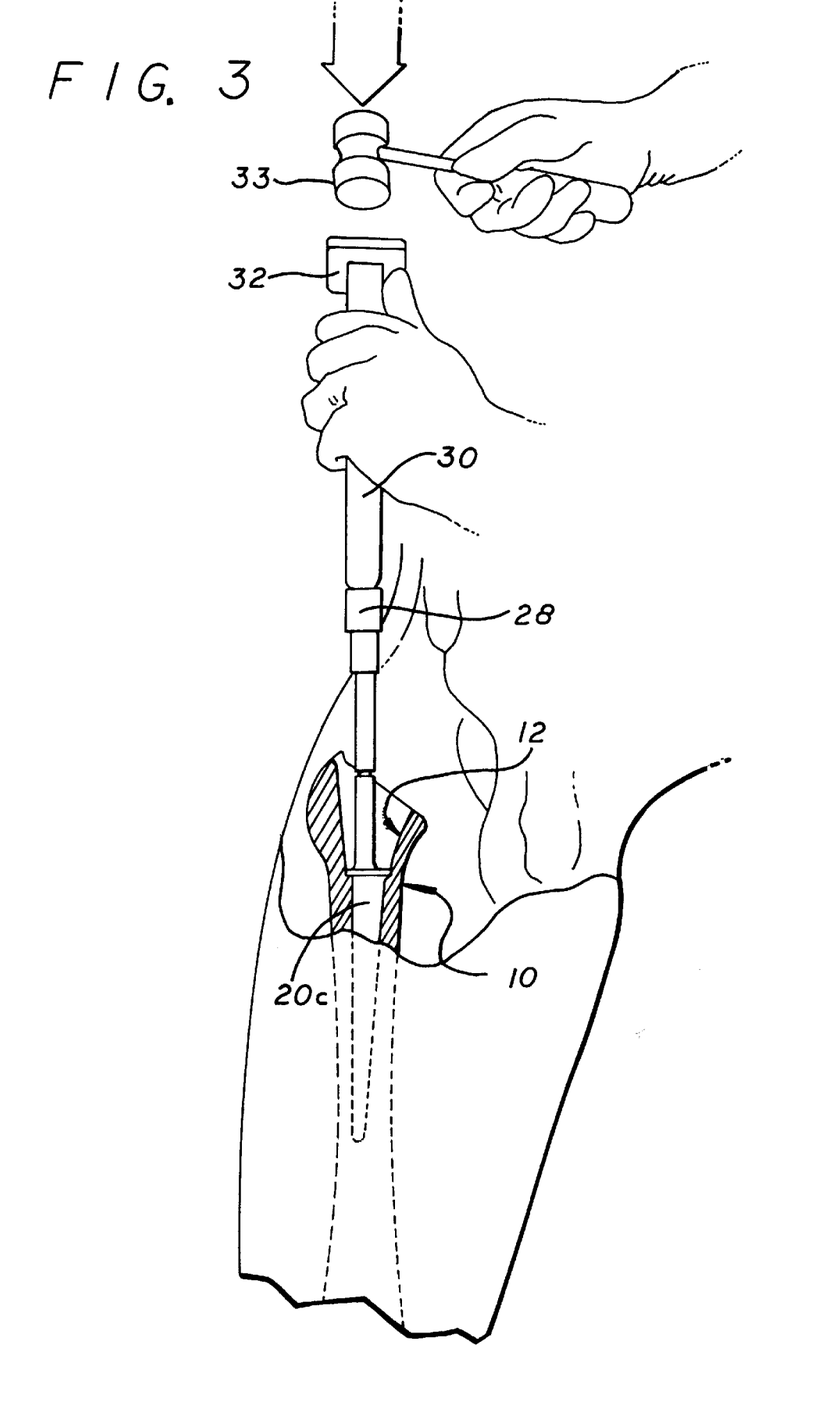
FIG. 3 is a schematic perspective view of apparatus for inserting, and driving, a tamp into the cavity in the femur.

The tops of the tamps 20a, 20b, 20c and 20d are provided with a detent 26 (FIG. 4) for coupling to a detent 28 (FIG. 3) on a handle 30. The handle 30 is provided with a cap 32 for receiving taps from a hammer 33 or similar driving member to force the individual one of the tamps 20a, 20b, 20c and 20d into the cavity 12. The individual ones of the tamps 20a, 20b, 20c and 20d are forced progressively into the cavity 12 by applying the hammer 33 a number of successive times against the cap 32 on the handle 30.

The cavity 12 may initially be formed in the femur 10 and the bone fragments 16 may then be disposed in the cavity. The tamp 20a may then be inserted into the cavity 12 with the detent 28 on the handle 30 coupled to the detent 26 at the upper end of the tamp. The tamp 20a is then driven progressively into the cavity 12 by applying successive driving forces (as by the hammer 33 ) to the cap 32 on the handle. This progressive movement of the tamp 20a into the cavity 12 continues until the groove 24a becomes substantially aligned with the top of the femur 10.

When the groove 24a in the tamp 20a becomes substantially aligned with the top of the femur 10, the collar 22a substantially abuts the femur inner walls defining the cavity 12. At this position, the bone fragments 16 are tightly packed against one another and against the collar 22a on the tamp 20a and against the femur 10. The tight packing occurs in the horizontal and vertical directions. The horizontal and vertical directions may be considered as respectively equivalent to radial and axial directions. This is shown schematically in FIG. 11. This tight packing of the bone fragments 16 in the cavity 12 causes blood and tissue fluids to be squeezed from the cavity 12.

The tamp 20a is then withdrawn from the cavity. The bone fragments 16 remain tightly packed against one another and the femur 10 even after the tamp 20 is withdrawn from the femur. This results in part from the fact that the bone fragments 16 have irregular shapes so that the tight packing of these bone fragments in the horizontal and vertical directions causes the fragments to be tightly intercoupled.

The tamp 20 b is now inserted into the cavity 12 and the steps discussed in the last three (3) paragraphs are repeated to pack the bone fragments 16 tightly against one another in the horizontal and vertical directions and against the tamp and the femur 10. The bone fragments 16 become tightly packed in part because the collar 22b on the tamp 20b substantially abuts the inner walls of the femur 10 when the groove 20b in the tamp is at substantially the same vertical level as the top of the femur 10. As will be seen, however, the cumulative height of the tightly packed bone fragments 16 in the cavity 12 after the use of the tamp 20b is greater than the height of the tightly packed bone particles in the cavity after the use of the tamp 20a.

The tamp 20b is now withdrawn from the cavity 12. Even after the withdrawal of the tamp 20b from the cavity 12, the shape and the dimensions of the cavity 12 are preserved because of the tight packing of the bone particles in the cavity. The tamp 20c is then inserted into the cavity 12 and is driven into the cavity until the collar 20c abuts the inner walls of the femur 10. This causes the bone particles 16 to become tightly packed in the cavity 12 in a horizontal and vertical direction to a height greater than the height of the bone particles packed in the cavity by the tamp 20b.

The tamp 20c is then withdrawn from the cavity 12 and the tamp 20d is inserted, and driven, into the cavity. When the tamp 20d has been driven into the cavity 12, the bone fragments 16 become tightly packed to the top of the cavity as shown schematically in FIG. 13A.

After the tamp 20d has been withdrawn from the cavity 12, a suitable fluid binder 40 (FIG. 13B) such as a polymethyl/methacrylate acrylic bone cement is inserted into the cavity. The binder 40 permeates through a relatively short distance in the spaces between the tightly packed bone fragments 16 and between the bone fragments and the femur 10. This permeation of the binder 40 through only a relatively short distance between the bone fragments 16 results from the tight packing of the bone fragments. When solidified, the binder 40 facilitates the retention of the bone fragments in fixed positions in the femur 10. For example, a suitable binder may be obtained from Howmedica of East Rutherford, N.J., and from Zimmer of Warsaw, Ind.

The prosthesis 14 is inserted into the cavity 12 while the binder 30 is still in fluid form. The prosthesis 14 may be made from a suitable material such as a stainless steel. The prosthesis has a shape corresponding to the shape of the tamp 20d below the collar 22d. This may be seen from a comparison of the sections shown in FIGS. 15–18 with the sections respectively shown in FIGS. 7–10. When the binder 40 has solidified after a suitable period of time such as approximately fifteen (15) minutes, the prosthesis 14 is implanted with stability in the bone fragments 16 relative to the femur 10.

The width of the prosthesis 14 is preferably slightly less than the width of the tamp 20 at progressive positions in the cavity 12. This causes a layer 40 of the binder 30 to be disposed between the prosthesis 14 and the bone fragments 16. This layer may have a thickness of a few millimeters. The layer 40 additionally permeates into the bone fragments 16 for a limited distance such as approximately a few millimeters. This permeation distance is limited because of the tight packing of the bone fragments 16.

Figures 13B, 14, 15, 16, 17, 18:
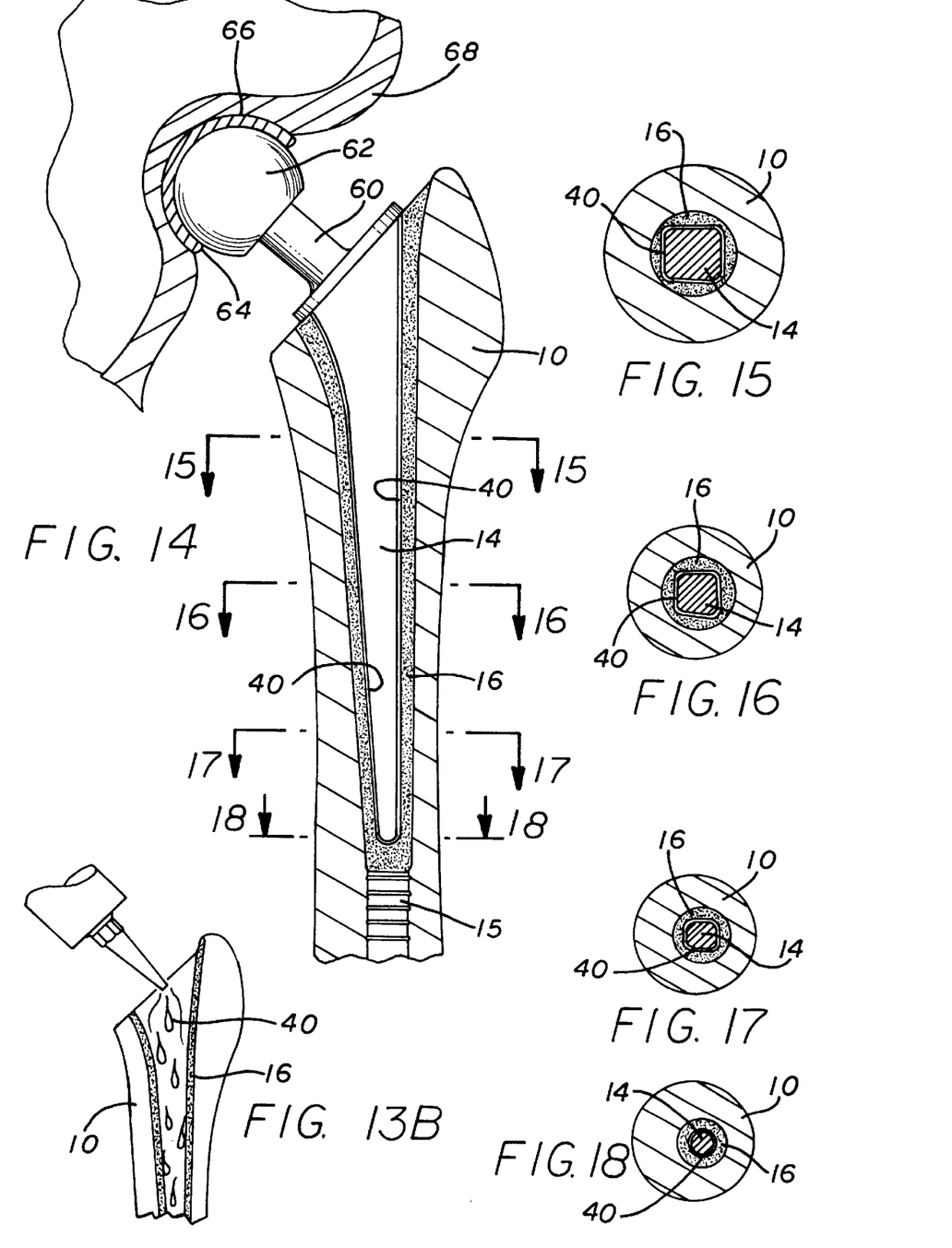
FIG. 13B is a schematic perspective view showing the insertion of a liquid binder into the femur cavity after the removal from the cavity of the tamp shown in FIG. 13A.
FIG. 14 is an enlarged fragmentary elevational view showing the prosthesis of FIG. 5 in the femur cavity and showing the coupling of the prosthesis to a hip bone.
FIGS. 15, 16, 17 and 18 are respectively sectional views taken substantially on the lines 15—15, 16—16, 17—17, and 18—18 of FIG. 14.

FIG. 14 schematically illustrates the hip prosthesis 14 after the hip prosthesis operation has been completed. As shown, the hip prosthesis 14 includes a stem 60 extending upwardly from the top of the prosthesis and supporting a substantially spherical member 62. A hemispherical coupling member 64 is supported on the spherical member 62. The hemispherical coupling member 64 is disposed in a hemispherical socket 66 disposed in a hip bone 68.

The prosthesis 14, the solidified bone fragments 16 and the femur 10 are able to withstand large forces applied to the femur. This results from the fact that the forces are minimized at each position because of the substantially uniform distribution of forces through a large volume as a result of the tight and substantially uniform packing of the base fragments 16. This tight packing of the bone fragments 16 causes the pressure exerted at each position to be relatively low.

Figures 4, 5, 6, 7, 8, 9, 10, 19:
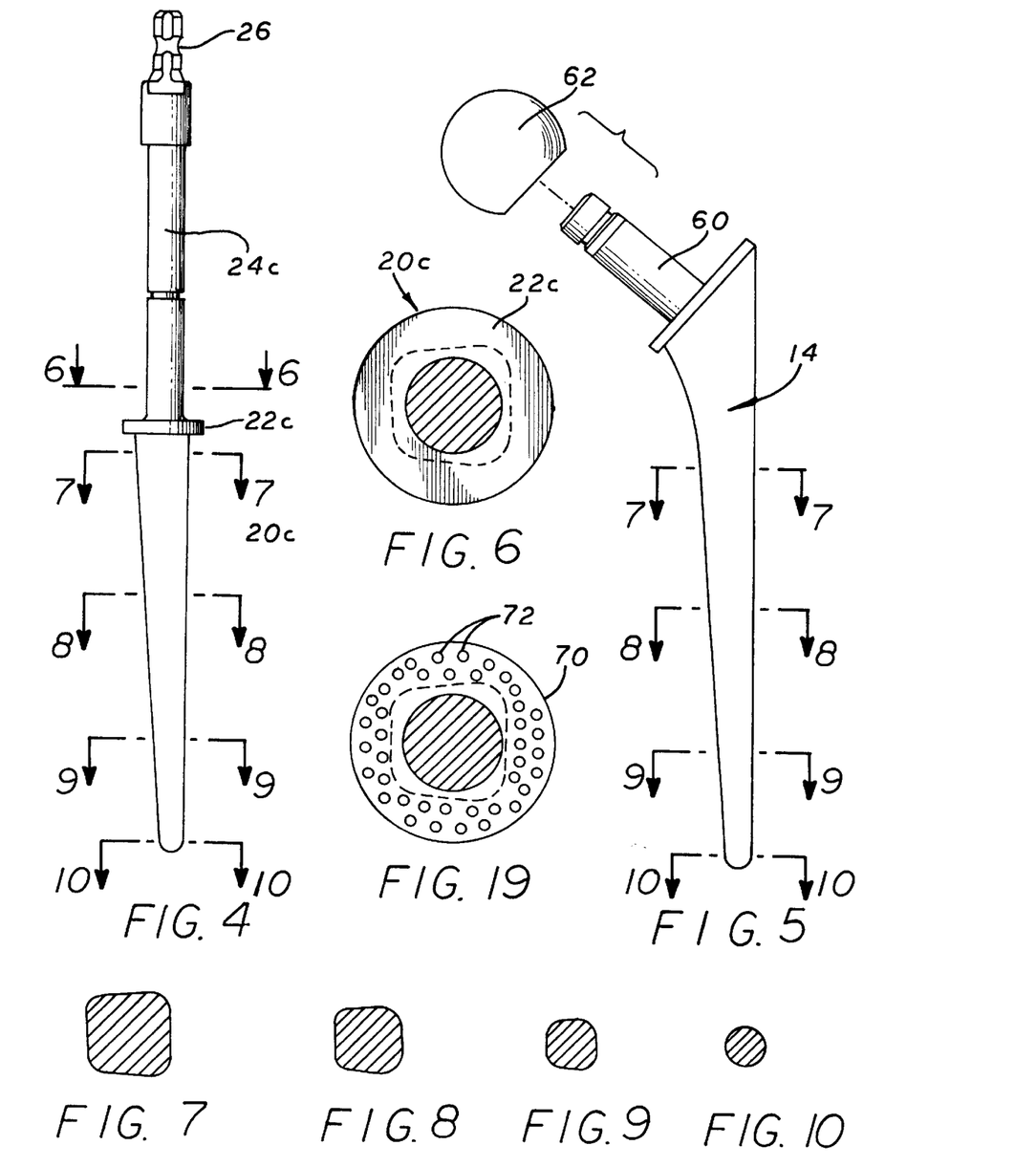
FIG. 4 is an enlarged elevational view of the tamp shown in FIG. 3.
FIG. 5 is an enlarged elevational view of a prosthesis having a shape along a portion of its length substantially corresponding to the shape of the tamp shown in FIGS. 3 and 4.
FIG. 6 is a sectional view of the tamp shown in FIGS. 3 and 4 and is taken substantially on the line 6—6 of FIG. 4.
FIGS. 7, 8, 9 and 10 are sectional views respectively taken substantially on the lines 7—7, 8—8, 9—9 and 10—10 of FIGS. 4 and 5.
FIG. 19 is a view of a modified collar on one of the tamps and is taken on a radial line corresponding substantially in position to the line 6—6 in FIG. 4.
Figure 11:
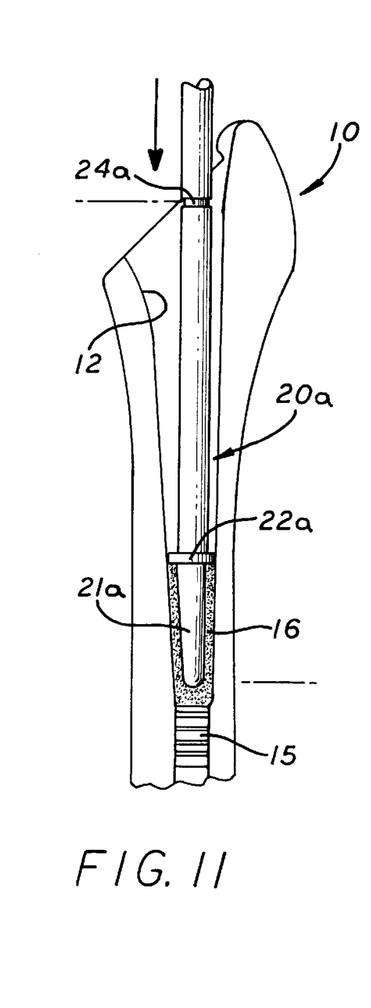
FIG. 11 is an enlarged fragmentary elevational view showing the disposition in the femur cavity of a first one of the tamps in a sequence and showing the packing of bone fragments to a first height in the cavity by such tamp.
Figure 12:
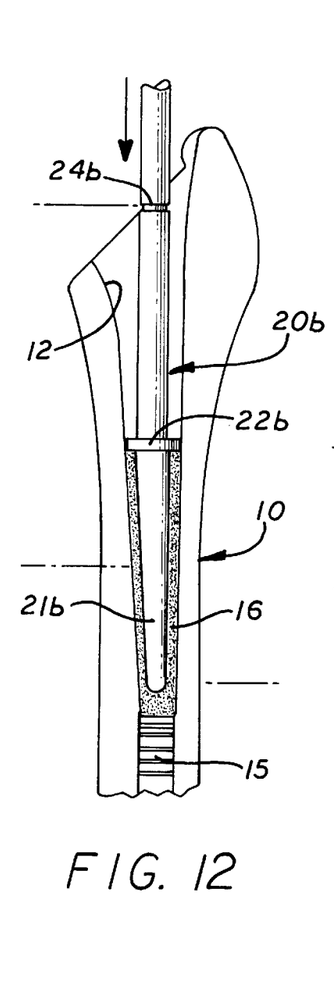
FIG. 12 is an enlarged fragmentary elevational view showing the disposition in the femur cavity of a second one of the tamps in a sequence and showing the packing by such tamp of the bone fragments to an increased height in the cavity.

FIG. 19 illustrates a tamp with a modified collar 70. The collar 70 is modified by providing a plurality of minuscule holes 72 in the collar. The holes 72 are large enough to provide for the escape of air and other fluid through such holes while the bone fragments 16 are being packed against one another by the collar 70. The holes 72 are sufficiently small to prevent the bone fragments 16 from passing upwardly and out of the holes while the bone fragments are being tightly packed by the application of forces against the collar.

Although this invention has been disclosed and illustrated with reference to particular embodiments, the principles involved are susceptible for use in numerous other embodiments which will be apparent to persons of ordinary skill in the art. The invention is, therefore, to be limited only as indicated by the scope of the appended claims.

I claim:

1. Apparatus for use with a femur in a hip replacement where the femur has a hollow cavity defined by inner walls in the femur and where bone particles are implantable in the hollow cavity in the femur, a tamp having an elongated shaft shaped to extend into the hollow cavity in the femur, the shaft having a collar at an intermediate position along the length of the shaft, the collar extending outwardly from the shaft in a direction transverse to the length of the shaft and being dimensional for disposition against the inner walls in the femur to provide for a packing of the bone particles in the hollow cavity in the femur in the space in the cavity below the collar.

2. Apparatus as set forth in claim 1 wherein:

a marking is provided on the shaft of the tamp at a position on the shaft to indicate that the tamp, after being driven into the hollow cavity in the femur, has been inserted into the proper depth in the femur.

3. Apparatus as set forth in claim 1 wherein:

a handle is attached to an upper end of the tamp and is provided with a cap at an upper end of the handle to receive forces for driving the tamp into the hollow cavity in the femur.

4. In combination, a femur having a hollow cavity defined by internal walls in the femur, bone particles disposed in the hollow cavity, and a plurality of tamps having characteristics for progressive disposition in the hollow cavity, each individual one of the tamps having an elongated shaft with a collar extending outwardly in a direction transverse to the length of the shaft at an intermediate position along the length of the shaft, the collar in each individual one of the tamps being disposed at an individual one of a plurality of progressive positions along the length of the hollow cavity to provide for the packing of the bone fragments to an individual one of the plurality of the progressive positions along the length of the hollow cavity.

5. In a combination as set forth in claim 4 wherein:

the collar on each individual one of the tamps has dimensions to fit snugly in the hollow cavity at the individual one of the plurality of progressive positions in the hollow cavity.

6. In a combination as set forth in claim 4 wherein:

the plurality of progressive positions constitute a first plurality of progressive positions and wherein;

each individual one of the tamps has a depth gauge marking at an individual one of a plurality of second progressive positions along the length of the individual one of the tamps to indicate when the individual one of the tamps has been driven into the cavity to the proper depth in the cavity.

7. In a combination as set forth in claim 4 wherein:

each individual one of the tamps is constructed at its upper end to receive a handle and wherein;

a handle is attachable to each individual one of the tamps at the upper end of the individual one of the tamps and wherein;

the handle is constructed to receive forces for driving each individual one of the tamps into the hollow cavity to provide for a packing of the bone fragments in the cavity.

8. In a combination as set forth in claim 7 wherein:

the collar on each individual one of the tamps has dimensions to fit snugly in the hollow cavity at the individual one of the plurality of progressive positions in the hollow cavity and wherein;

the plurality of progressive positions constitute a first plurality of progressive positions and wherein;

each individual one of the tamps has a depth gauge marking along the length of the individual one of the tamps at an individual one of a plurality of second progressive positions, dependent upon the length of such individual one of the tamps, to indicate when the individual one of the tamps has been driven into the cavity to the proper depth in the cavity.

9. In a method of providing for a prosthesis of a femur in a patient's hip, the steps of:

providing a cavity in the patient's femur, disposing a plurality of bone fragments in the femur cavity, providing a tamp having a shaft with a particular length, the shaft having a collar at an intermediate position along the particular length of the shaft and extending outwardly from the shaft in a direction transverse to the length of the shaft, inserting the tamp into the cavity after the disposition of the bone fragments in the cavity, and providing a controlled drive of the tamp into the cavity to pack the tamp against the bone fragments in the cavity.

10. In a method as set forth in claim 9, the additional steps of:

removing the tamp from the cavity, inserting a fluid binder into the cavity in contact with the packed particles in the cavity through a limited distance to provide for a retention of the packed particles in a fixed relationship to one another and to the inner walls of the femur, and inserting a prosthesis into the cavity after the disposition of the binder in the cavity.

11. In a method as set forth in claim 10 wherein:

the prosthesis is driven into the cavity after the insertion of the binder into the cavity to provide for the retention of the prosthesis in a fixed relationship to the bone particles in the femur and the inner walls of the femur.

12. In a method as set forth in claim 9 wherein:

the collar on the tamp has dimensions to fit snugly in the cavity against the inner walls of the femur when the tamp has been driven a particular distance into the cavity.

13. In a method as set forth in claim 9 wherein:

a marking is provided on the tamp to indicate relative to the top of the femur when the tamp has been driven into the cavity through a particular distance.

14. In a method as set forth in claim 9 wherein:

a space is provided in the cavity between the prosthesis and the bone fragments and wherein;

the binder is inserted into the space between the prosthesis and the bone fragments to bind the prosthesis to the bone fragments.

15. In a method as set forth in claim 14 wherein:

the binder permeates the bone fragments through a limited distance along the length of the prosthesis.

16. In a method as set forth in claim 9, including the steps of:

the collar on the tamp having dimensions to fit snugly against the inner wall of the femur when the tamp has been driven a particular distance into the cavity, providing a marking on the tamp to indicate relative to the top of the femur when the tamp has been driven into the cavity through a distance providing the snug relationship between the collar and the inner walls of the femur, removing the tamp from the cavity, inserting a fluid binder into the cavity in contact with the packed particles in the cavity and in contact with the inner walls in the femur to retain the packed particles in a fixed relationship to one another and to the inner walls of the femur, and inserting a prosthesis into the cavity after the insertion of the binder into the cavity.

17. In a method as set forth in claim 16 wherein:

a space is provided in the cavity between the prosthesis and the bone fragments and wherein;

the binder is inserted into the space between the prosthesis and the bone fragments to bind the prosthesis to the bone fragments and wherein;

the binder permeates the bone fragments through a limited distance along the length of the prosthesis.

18. In a method of providing a prosthesis in a femur in a patient's hip, the steps of:

providing a cavity in the patient's femur, progressively inserting bone fragments into the cavity, providing a plurality of tamps, each having a shaft with a bottom and having a collar extending radially outwardly from the shaft at an individual distance from the bottom of the shaft to provide for the disposition of such collar at an individual one of a plurality of progressive positions in the cavity, and inserting the tamps in sequence into the cavity in accordance with the relative distances of the collar on each of such tamps from the bottom of the shaft on the tamp to provide for the packing of progressive amounts of the bone fragments in the space in the cavity below the collars on the tamps.

19. In a method as set forth in claim 18, the step of:

driving each of the tamps into the cavity, after the insertion of the tamp into the cavity, to pack the bone particles in the cavity against the collar on the tamp and against one another and against the femur.

20. In a method as set forth in claim 18 wherein:

the tamps are driven into the cavity in a sequence involving progressive increases in the distance between the bottoms of the tamps and the positions of the collars on the tamps and wherein;

each of the tamps is driven into the cavity to provide for a packing of the collar on such tamp against the bone fragments in the cavity and wherein;

each tamp is removed from the cavity after such packing of the bone fragments in the cavity and the next tamp in the sequence is inserted into the cavity to provide for a packing of the particles in the cavity.

21. In a method as set forth in claim 18 wherein:

the cavity is defined by inner walls in the femur and wherein;

the radial dimensions of the cavity progressively increase at progressive distances from the bottom of the cavity and wherein;

the radial dimensions of the collars on the progressive tamps in the sequence progressively increase to provide a substantially snug relationship between the collars in the sequence and the inner walls of the femur at the progressive distances in the cavity from the bottom of the cavity.

22. In a method as set forth in claim 18 wherein:

the prosthesis is inserted into the cavity in the femur after the removal of the last one of the tamps in the sequence from the cavity and wherein;

the prosthesis is driven into the cavity after its insertion into such cavity.

23. In a method as set forth in claim 19 wherein:

the tamps are inserted into the cavity in a sequence involving progressive increases in the distance between the bottom of the cavity and the positions of the collars on the tamps and wherein;

each of the tamps is driven into the cavity after the insertion of the tamp into the cavity to provide for a packing of the collar on the tamp against the bone fragments in the cavity and wherein;

each tamp is removed from the cavity and the next tamp in the sequence is inserted into the cavity to provide for a packing of the collar on such tamp against the bone fragments in the cavity and wherein;

the cavity is defined by inner walls in the femur and wherein;

the radial dimensions of the cavity progressively increase at progressive distances from the bottom of the cavity and wherein;

the radial dimensions of the collars on the progressive tamps in the sequence progressively increase to provide a substantially snug relationship between the collars in the sequence and the inner walls of the femur at the progressive distances in the cavity from the bottom of the cavity and wherein;

the prosthesis is inserted into the cavity in the femur after the removal of the last one of the tamps in the sequence from the cavity and wherein;

the prosthesis is driven into the cavity after its insertion into such cavity.

24. In a method as set forth in claim 18 wherein:

the radial dimension of the prosthesis at progressive positions along the prosthesis is less than the radial dimension of the cavity to define a space at such progressive positions between the prosthesis and the bone fragments and wherein;

a binder is inserted into such space to bind the bone fragments to the prosthesis.

25. In a method as set forth in claim 24 wherein:

the binder permeates through a limited distance into the space between the bone fragments.

26. In a method as set forth in claim 23 wherein:

the radial dimension of the prosthesis at progressive positions along the prosthesis is less than the radial dimension of the cavity to define a space at such progressive positions between the prosthesis and the bone fragments and wherein;

a binder is inserted into such space to bind the bone fragments to the prosthesis and wherein;

the binder permeates through a limited distance into the space between the bone fragments.

27. In a method of providing for a prosthesis of a femur in a patient's hip, the steps of:

providing a cavity in the patient's femur, packing bone fragments into the cavity at progressive incremental heights in the cavity while maintaining the shape of the cavity during such packing to substantially receive the prosthesis, and inserting the prosthesis into the cavity after the bone fragments have been packed into the cavity at the progressive incremental heights.

28. In a method as set forth in claim 27 wherein:

the bone fragments are packed at progressive incremental heights in the cavity to the top of the cavity while maintaining the shape of the cavity during such packing to subsequently receive the prosthesis.

29. In a method as set forth in claim 27 wherein:

a fluid binder having properties of hardening is inserted into the cavity after the packing of the bone fragments in the cavity to the top of the cavity and before the insertion of the prosthesis into the cavity.

30. In a method as set forth in claim 29 wherein:

the prosthesis is inserted into the cavity after the insertion of the fluid binder into the cavity.

31. In a method as set forth in claim 29 wherein:

the prosthesis is narrower than the cavity at progressive positions along the cavity to define a space between the prosthesis and the cavity and wherein:

the fluid binder is inserted into the space between the prosthesis and the cavity.

32. In a method as set forth in claim 31 wherein:

the binder permeates through a limited distance into the space between the bone fragments.

33. In a method as set forth in claim 28 wherein:

a fluid binder having properties of hardening is inserted into the cavity after the packing of the bone fragments in the cavity to the top of the cavity and before the insertion of the prosthesis into the cavity and wherein;

the prosthesis is inserted into the cavity after the insertion of the fluid binder into the cavity and wherein;

the prosthesis is narrower than the cavity at progressive positions along the cavity to define a space between the prosthesis and the cavity and wherein;

the fluid binder is inserted into the space between the prosthesis and the cavity and wherein;

the binder permeates through a limited distance into the space between the bone fragments.

* * * * *

UNITED STATES PATENT AND TRADEMARK OFFICE
CERTIFICATE OF CORRECTION

PATENT NO. : 5,910,172
DATED : Jun. 8, 1999
INVENTOR(S) : Brad L. Penenberg

It is certified that error appears in the above-identified patent and that said Letters Patent is hereby corrected as shown below:

Column 3, line 53, change "22d" second occurrence, to read --20d--.

Column 4, line 62, change "20b", to read --24b--.

Column 5, line 6, change "20c", to read --22c--.

Column 5, line 30, change "30", to read --40--.

Column 5, line 42, delete "40" after "layer", and after "binder", change "30", to read --40--.

Column 5, line 45, change "layer", to read --binder--.

Signed and Sealed this

Fourteenth Day of March, 2000

Attest:

Q. TODD DICKINSON

*Attesting Officer*  *Commissioner of Patents and Trademarks*

UNITED STATES PATENT AND TRADEMARK OFFICE
CERTIFICATE OF CORRECTION

PATENT NO. : 5,910,172
DATED      : Jun. 8, 1999
INVENTOR(S) : Brad L. Penenberg It is certified that error appears in the above-identified patent and that said Letters Patent is hereby corrected as shown below:

Column 3, line 19, change "cancerous", to read --cancellous--.

Column 3, line 21, change "cancerous", to read --cancellous--.

Signed and Sealed this

Tenth Day of April, 2001

Attest:

NICHOLAS P. GODICI

Attesting Officer     Acting Director of the United States Patent and Trademark Office